United States Patent
Chang et al.

(10) Patent No.: US 10,485,461 B2
(45) Date of Patent: Nov. 26, 2019

(54) APPARATUS AND METHOD FOR ESTIMATING SUBSTANCE IN BLOOD

(71) Applicant: SAMSUNG ELECTRONICS CO., LTD., Suwon-si (KR)

(72) Inventors: Ki Young Chang, Yongin-si (KR); Jung Yong Nam, Hwaseong-si (KR); Joon Hyung Lee, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 314 days.

(21) Appl. No.: 15/400,481

(22) Filed: Jan. 6, 2017

(65) Prior Publication Data

US 2018/0028097 A1    Feb. 1, 2018

(30) Foreign Application Priority Data

Jul. 29, 2016  (KR) ........................ 10-2016-0097358

(51) Int. Cl.
*A61B 5/00* (2006.01)
*A61B 5/1455* (2006.01)
(Continued)

(52) U.S. Cl.
CPC .............. *A61B 5/1455* (2013.01); *A61B 5/01* (2013.01); *A61B 5/14532* (2013.01);
(Continued)

(58) Field of Classification Search
CPC ... A61B 5/1455; A61B 5/6824; A61B 5/7221; A61B 5/7267; A61B 5/14546; A61B 5/14532; A61B 5/4872; A61B 5/7246; A61B 2562/0238; G01N 21/49; G01N 21/359

See application file for complete search history.

(56) References Cited

U.S. PATENT DOCUMENTS 5,795,305 A   8/1998   Cho et al.
6,190,315 B1  2/2001   Kost et al.
(Continued)

FOREIGN PATENT DOCUMENTS

JP   2004-226277 A   8/2004
JP   2012-68263 A    4/2012
(Continued)

OTHER PUBLICATIONS

Ahn et al., "Blood Glucose Measurement Principles of Noninvasive Blood Glucose Meter: Focused on the Detection Methods of Blood Glucose", Journal of Biomedical Engineering Research, vol. 33, 2012, pp. 114-127.
(Continued)

*Primary Examiner* — Christian Jang
(74) *Attorney, Agent, or Firm* — Sughrue Mion, PLLC

(57) ABSTRACT

An apparatus for estimating a substance in blood in a noninvasive manner is provided. The apparatus includes a light source configured to emit light to skin of a user; a plurality of detectors which are disposed at different distances from the light source and configured to detect light signals from the light returning from the skin; and a processor configured to determine a similarity between at least two light signals among the detected light signals and estimate the substance in blood based on the similarity.

13 Claims, 22 Drawing Sheets

(51) Int. Cl.
*A61B 5/01* (2006.01)
*A61B 5/145* (2006.01)
*G01N 21/359* (2014.01)
*G01N 21/49* (2006.01)

(52) U.S. Cl.
CPC ........ *A61B 5/14546* (2013.01); *A61B 5/4872* (2013.01); *A61B 5/681* (2013.01); *A61B 5/6824* (2013.01); *A61B 5/7221* (2013.01); *A61B 5/7246* (2013.01); *A61B 5/7267* (2013.01); *G01N 21/359* (2013.01); *G01N 21/49* (2013.01); *A61B 2562/0238* (2013.01)

(56) References Cited

U.S. PATENT DOCUMENTS

| | | |
|---|---|---|
| 6,990,364 B2 | 1/2006 | Ruchti et al. |
| 7,003,337 B2 | 2/2006 | Harjunmaa et al. |
| 7,066,884 B2 | 6/2006 | Custer et al. |
| 7,206,623 B2 | 4/2007 | Blank et al. |
| 7,565,249 B2 | 7/2009 | Kraemer et al. |
| 8,102,525 B2 | 1/2012 | Guo et al. |
| 8,224,414 B2 | 7/2012 | Kellogg et al. |
| 8,287,483 B2 | 10/2012 | Mitragotri et al. |
| 8,870,810 B2 | 10/2014 | Mitragotri et al. |
| 2002/0045808 A1* | 4/2002 | Ford .................. G16H 10/40 600/347 |
| 2004/0171980 A1 | 9/2004 | Mitragotri et al. |
| 2006/0015058 A1 | 1/2006 | Kellogg et al. |
| 2006/0094944 A1 | 5/2006 | Chuang |
| 2006/0094945 A1 | 5/2006 | Barman et al. |
| 2008/0311670 A1 | 12/2008 | Zhu |
| 2010/0210926 A1 | 8/2010 | Ciancitto et al. |
| 2012/0330164 A1 | 12/2012 | Ermakov et al. |
| 2014/0005505 A1 | 1/2014 | Peyser et al. |
| 2015/0011849 A1* | 1/2015 | Ruchti ................. A61B 5/1455 600/316 |
| 2015/0230743 A1 | 8/2015 | Silveira et al. |
| 2015/0313516 A1 | 11/2015 | Shimizu et al. |
| 2016/0015301 A1 | 1/2016 | Elliott et al. |
| 2016/0045151 A1 | 2/2016 | Lee et al. |

FOREIGN PATENT DOCUMENTS

| | | |
|---|---|---|
| KR | 10-1231455 B1 | 2/2013 |
| KR | 10-1494902 B1 | 2/2015 |
| KR | 10-2016-0019776 A | 2/2016 |
| WO | 95/15711 A1 | 6/1995 |
| WO | 2014/087825 A1 | 6/2014 |

OTHER PUBLICATIONS

Communication issued by the European Patent Office dated Aug. 28, 2017 in counterpart European Patent Application No. 17154532.0.

Communication dated Aug. 8, 2018, issued by the European Patent Office in counterpart European Patent Application No. 17154532.0.

* cited by examiner

APPARATUS AND METHOD FOR ESTIMATING SUBSTANCE IN BLOOD

CROSS-REFERENCE TO RELATED APPLICATION(S)

This application claims priority from Korean Patent Application No. 10-2016-0097358, filed on Jul. 29, 2016, in the Korean Intellectual Property Office, the disclosure of which is incorporated herein by reference in its entirety.

BACKGROUND

1. Field

Apparatuses and methods consistent with exemplary embodiments relate to estimating substances in blood using a noninvasive method.

2. Description of Related Art

An optical measurement method based on an infrared (Ir) ray or near infrared ray (NIR) may be used to estimate a level of a particular substance included in blood, for example, a blood sugar level or a neutral fat level in blood. When such an optical measurement method is used, it is possible to estimate a level of a particular substance which exists in a subject (e.g., human) in a non-invasive manner. As an example of the optical measurement method described above, there is a method of measuring and analyzing a scattered light signal.

SUMMARY

According to an aspect of an exemplary embodiment, there is provided an apparatus for estimating a substance in blood including: a light source configured to emit light to skin of a user; a plurality of detectors which are disposed at different distances from the light source and configured to detect light signals from the light returning from the skin; and a processor configured to determine a similarity between at least two light signals among the detected light signals and estimate the substance in blood based on the similarity.

The processor may include a similarity calculator which determined the similarity between waveforms of the at least two light signals based on a time axis.

The similarity may include at least one of Euclidean distance, Pearson correlation coefficient, Spearman correlation coefficient, and a cosine similarity.

The light source may include a near infrared (NIR) light emitting diode (LED) light source.

The processor may include a similarity determiner configured to determine whether the determined similarity is greater than or equal to a reference similarity; and a substance-in-blood estimator configured to estimate the substance based on the detected light signals when the reference similarity is greater than or equal to the reference similarity.

The processor may further include a redetection controller which controls to redetect light signals returning from the skin of the user when the reference similarity is less than the reference similarity.

The substance-in-blood estimator may determine scattering coefficients using light signals which have a similarity greater than the reference similarity, and obtain a level of the substance in blood based on the scattering coefficients and a correlation model.

When a number of the detected light signals that are equal to or greater than the reference similarity is three or greater, the substance-in-blood estimator may select two light signals from the detected light signals based on similarities among the detected light signals and estimates the substance in blood using the selected two light signals.

The processor may further include a reference manager which updates reference information which includes at least one of the reference similarity and a correlation model.

The reference manager may aggregate the number of times that the determined similarity is less than the reference similarity and may update the reference information when the aggregated number exceeds a threshold.

The reference manager may collect learning data using the detected light signals and may update the reference information based on the collected learning data.

The apparatus may further include a communicator which is connected to an external apparatus and receives a reference value of the substance in blood measured from the blood of the user. Here, the reference manager may update the reference information further based on the received reference value of the substance in blood.

The substance in blood may include at least one of blood sugar, cholesterol, neutral fat, a skin temperature, protein, and uric acid.

The apparatus may further include an outputter which outputs a result of estimating the substance in blood to the user.

According to an aspect of another exemplary embodiment, there is provided a method of estimating a substance in blood including: emitting light to skin of a user; detecting light signals from the light returning from the skin, at a plurality of different positions; determining a similarity between at least two light signals among the detected light signals; and estimating the substance in blood based on the similarity.

The method may further include determining whether the determined similarity is greater than or equal to a reference similarity. Here, the estimating the substance in blood may include estimating the substance in blood based on the detected light signals when the reference similarity is greater than or equal to the reference similarity.

The method may further include controlling to redetect light signals from the skin of the user when the reference similarity is less than the reference similarity.

The estimating the substance in blood may include calculating scattering coefficients using light signals which have a similarity greater than the reference similarity; and obtaining a level of the substance in blood based on the calculated scattering coefficients and a correlation model.

The method may further include updating reference information which includes at least one of the reference similarity and a correlation model.

The updating the reference information may include aggregating the number of times that the determined similarity is less than the reference similarity that the reference similarity and updating the reference information when the aggregated number exceeds a threshold.

The updating the reference information may further include collecting learning data using the detected light signals and updating the reference information based on the collected learning data.

The method may further include outputting a result of estimating the substance in blood to the user.

According to an aspect of another exemplary embodiment, there is provided a wearable device including a device body, a detection sensor which is disposed on the device body and detects light signals reflected from skin of a user; and a processor which is disposed on the device body and is configured to determine similarities among the detected light signals, and estimate a substance in blood based on the determined similarities.

The detection sensor may include a single light source which emits light to the skin of the user and a plurality of detectors which detect the light signals from the light returning from the skin.

The processor may determine whether the determined similarities are equal to or greater than a reference similarity, may estimate the substance in blood based on the detected light signals when the determined similarities are equal to or greater than the reference similarity, and may control the detection sensor to redetect light signals when the determined similarities are less than the reference similarity.

The processor may operate the detection sensor in one of a mode for estimating a substance in blood and a reference management mode.

The wearable device may further include a communicator which is mounted on the device body and is connected to an external apparatus to receive a substance-in-blood reference value measured from blood of the user when the detection sensor operates in the reference management mode.

The wearable device may further include a displayer which is mounted on the device body and displays a result of estimating the substance in blood.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
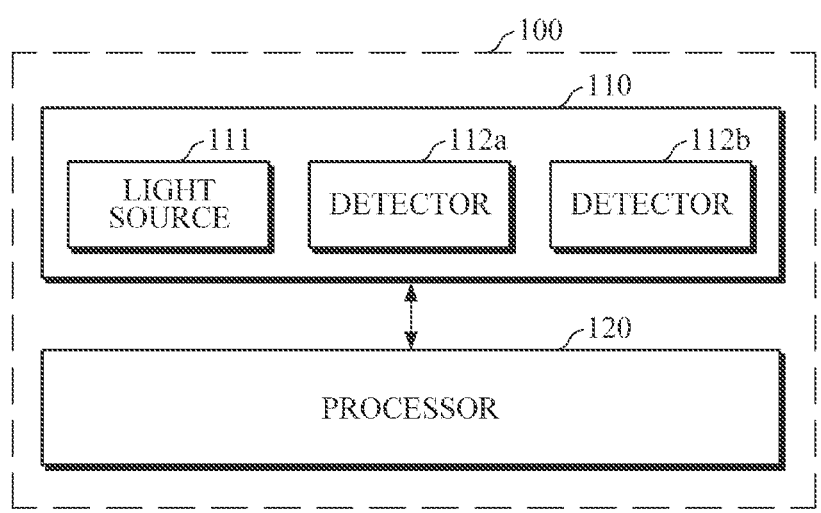
FIG. 1 is a block diagram illustrating an example of an apparatus for estimating a substance in blood.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Although terms such as first, second, etc. may be used to describe various elements, the elements should not be limited thereby. The terms are used only for distinguishing one element from others. Singular expressions, unless contextually otherwise defined, include plural expressions. Also, when it is described that a part "includes" an element, unless defined otherwise, it means that the part does not exclude other elements but may further include other elements. Also, the terms "portion", "module", etc. specified herein mean a unit which performs at least one function or operation and may be embodied as hardware, software, or a combination of hardware and software.

Expressions such as "at least one of," when preceding a list of elements, modify the entire list of elements and do not modify the individual elements of the list.

FIG. 1 is a block diagram illustrating an example of an apparatus for estimating a substance in blood. An apparatus for estimating a substance in blood may be mounted on a wearable device which a user wears on. The wearable device includes various types such as a watch type, a bracelet type, a wristband type, a ring type, a glasses type, a hair band type, etc. and is not particularly limited in shape or size, etc.

Referring to FIG. 1, the apparatus 100 for estimating a substance in blood includes an optical measurer 110 and a processor 120.

The optical measurer 110 may include a light source 111 and a plurality of detectors 112a and 112b. The light source 111 and the detectors 112a and 112b may be embodied as a single sensor or separate sensors.

The light source 111 emits light to the skin of a user according to a certain control signal. Here, the light source 111 may be formed as a single light source which emits light in a near infrared ray (NIR) band with a wavelength of 850 nm but is not limited thereto. Also, the light source 111 may include a light emitting diode (LED) or a laser diode. Here, a skin area of the user in close contact with the light source 111 may be the back of a hand or wrist, or an area adjacent to the surface of the wrist where a capillary vessel passes.

The detectors 112a and 112b are located at different distances from the light source 111 and detect light scattered and returned from skin tissue. The detectors 112a and 112b may include a photo diode, a photo transistor (PTr), or a charge-coupled device (CCD). For convenience of description, FIG. 1 illustrates only two detectors 112a and 112b arranged side by side but there is no particular limit in the number and arrangement of detectors.

For example, the light source 111 and the detectors 112a and 112b may be arranged side by side in an area corresponding to venous blood. The light emitted by the light source 111 passes through the skin of the user, arrives at the inside of the venous blood, is scattered by, for example, chylomicronemia particles containing neutral fat, and passes through the skin to return. A first detector 112a may be disposed at position p1 and a second detector 112b may be disposed at position p2. The position p1 may be closer to the light source 111 than the position p2. The first detector 112a and the second detector 112b may detect light signals R1 and R2 scattered from the skin and may measure average intensities R(p1) and R(p2) of the detected light signals.

According to an exemplary embodiment, the optical measurer 110 may be implemented as a spectrometer.

The processor 120 may receive data of the scattered light signals detected from the detectors 112a and 112b and may estimate a substance in blood using the received scattered light signal data. Here, the substance in blood may include blood sugar, cholesterol, neutral fat, a skin temperature, protein, uric acid, etc. but is not limited thereto. Hereinafter, for convenience of description, neutral fat will be described as an example as necessary.

When the scattered light signals R1 and R2 are detected from the first detector 112a and the second detector 112b, the processor 120 may determine whether the data of the detected scattered light signals R1 and R2 have a certain degree of reliability for estimating the substance in blood. When the data is reliable for estimating the substance in blood as a result of the determination, the processor 120 may estimate the substance in blood using the data of the detected scattered light signals R1 and R2. Otherwise, the scattered light signals may be measured again by controlling the optical measurer 110.

Figure 2A:
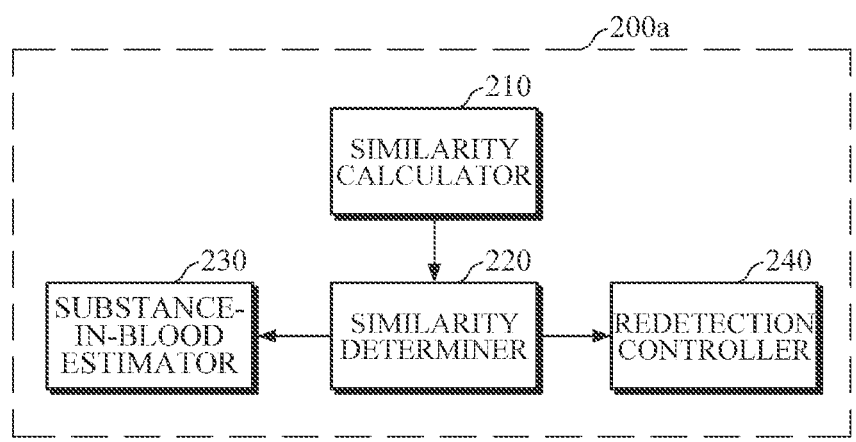
FIGS. 2A and 2B are block diagrams illustrating examples of a processor of FIG. 1.
Figure 2B:
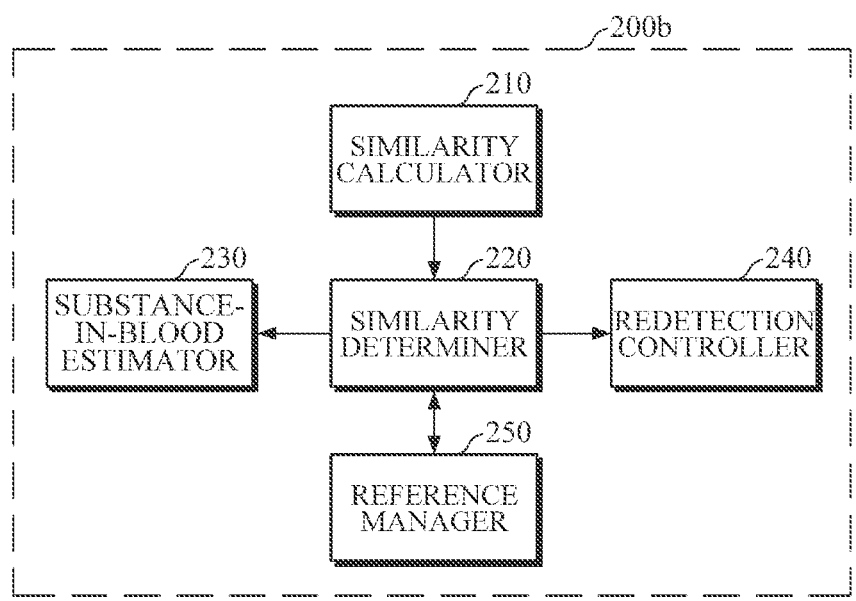

FIGS. 2A and 2B are block diagrams illustrating examples of the processor 120 of FIG. 1.

Referring to FIG. 2A, a processor 200a according to one example may include a similarity calculator 210, a similarity determiner 220, a substance-in-blood estimator 230, and a redetection controller 240.

When scattered light signals are detected by the detectors 112a and 112b, the similarity calculator 210 may calculate a similarity between the detected scattered light signals using a similarity calculation algorithm. Here, the similarity calculation algorithm may include a Euclidean distance, a Pearson correlation coefficient, a Spearman correlation coefficient, a cosine similarity algorithm, etc.

For example, the similarity calculator 210 may calculate a similarity between a waveform of a scattered light signal R1 detected by the first detector 112a and a waveform of a scattered light signal R2 detected by the second detector 112b based on a time axis using the cosine similarity algorithm. A cosine similarity means a similarity between two vectors measured using a cosine value of an angle between the two vectors of an internal space. The cosine value is 1 when the angle is 0 degree, and cosine values of other angles are smaller than 1. Accordingly, when using the cosine similarity, it is possible to determine a directional similarity of scattered light signal waveforms on a time axis.

When a similarity between the detected two scattered light signals R1 and R2 is calculated, the similarity determiner 220 may compare the calculated similarity to a reference similarity (e.g., predetermined value). Here, the reference similarity may be preset as a data reliability threshold according to a used similarity calculation algorithm or user properties, for example, a health condition, a measurement position, etc. When the calculated similarity is the preset threshold or greater, the similarity determiner 220 may determine that the detected scattered light signals are reliable for estimating the substance in blood. On the contrary, when the calculated similarity is less than the preset threshold, it may be determined that redetection of the scattered light signals is necessary.

When the detected scattered light signals are reliable for estimating the substance in blood as a result of the determination, the substance-in-blood estimator 230 may estimate the substance in blood by extracting scattering signal information from the detected scattered light signals. For example, the substance-in-blood estimator 230 may calculate scattering coefficients using intensities $R(p1)$ and $R(p2)$ of the scattered light signals detected by the first detector 112a and the second detector 112b and may estimate the substance in blood using the calculated scattering coefficients.

A scattering coefficient indicates a numerical value of light intensity reduced by scattering when light emitted by a light source moves a unit distance and may be defined as a ratio $R(p1)/R(p2)$ of the intensity of the scattered light signals detected by the first detector 112a and the second detector 112b or as a value proportional to the ratio. Also, the scattering coefficient may be calculated considering a distance p1 between the first detector 112a and the light source 111 and a distance p2 between the second detector 112b and the light source 111. An algorithm for calculating the scattering coefficient is not particularly limited and may be variously determined considering elements described above.

When the scattering coefficient is calculated, the substance-in-blood estimator 230 may estimate the substance in blood using the scattering coefficient and a previously generated correlation model. Here, the correlation model may be previously generated as a mathematical algorithm or a matching table which indicates a correlation between the scattering coefficient and the level of the substance in blood.

When the detected scattered light signal is unreliable for estimating the substance in blood as the result of the determination of the similarity determiner 220, the redetection controller 240 generates a control signal to control the optical measurer 110 to measure scattered light signals again.

Meanwhile, when there are three or more detectors, three or more scattered light signals may be detected. Here, the substance-in-blood estimator 230 may select two light signals based on similarities among the light signals and may estimate the substance in blood by using the selected two light signals.

For example, when three scattered light signals R1, R2, and R3 are detected, the similarity calculator 210 may calculate a similarity between each two scattered light signals R1-R2, R1-R3, and R2-R3 to calculate similarities C1, C2, and C3 thereof. The similarity determiner 220 may determine whether each of the similarities C1, C2, and C3 satisfies the reference similarity when the similarities C1, C2, and C3 are greater than or equal to the reference similarity. Here, a different reference similarity may be applied to each of the similarities C1, C2, and C3. When the similarities C1 and C2 satisfy the reference similarity and the similarity C1 is relatively greater than the similarity C2, the substance-in-blood estimator 230 may estimate the substance in blood using the light signals R1 and R2 of the similarity C1.

Referring to FIG. 2B, a processor 200b according to another example may include the similarity calculator 210, the similarity determiner 220, the substance-in-blood estimator 230, the redetection controller 240, and a reference manager 250. Since the similarity calculator 210, the similarity determiner 220, the substance-in-blood estimator 230, and the redetection controller 240 have been described in detail with reference to FIG. 2A, a configuration of the reference manager 250 will be mainly described below.

The reference manager 250 may manage reference information such as a reference similarity to be applied to a user and a correlation model. Here, reference information such as a reference similarity, a correlation model, etc. may be stored in a storage device. The storage device may include at least one of a flash memory type memory, a hard disk type memory, a multimedia card micro type memory, a card type memory such as a secure digital (SD) memory, an extreme digital (XD) memory, etc., a random access memory (RAM), a static random access memory (SRAM), a read-only memory (ROM), an electrically erasable programmable read-only memory (EEPROM), a programmable read-only memory (PROM), a magnetic memory, a magnetic disk, an optical disk, etc. Also, the storage device may be installed in the apparatus 100 for estimating a substance in blood or may be embodied as a portable external device.

The reference manager 250 may control the optical measurer 110 to sequentially measure a scattered light signal at a predetermined time interval, for example, 15 minutes for a predetermined time, for example, four hours to collect learning data necessary for updating reference information. Here, the user may allow a scattered light signal to be measured after eating a high-fat diet. Also, the scattered light signal data detected for each predetermined time may be collected by the optical measurer 110 as the learning data and the reference information may be generated or updated based on the collected learning data.

The reference manager 250 may use the collected learning data and a substance-in-blood reference value actually measured from a blood sample of the user. For example, the reference manager 250, as described with reference to following FIGS. 5A to 5C, may calculate a scattering coefficient using two scattered light signals sequentially detected for each predetermined time interval by the first detector 112a and the second detector 112b and may derive a correlation between the calculated scattering coefficient and an actual substance-in-blood numerical value. Also, based on the derived correlation, a correlation model between the scattering coefficient and the substance-in-blood numerical value may be obtained.

According to one exemplary embodiment, the reference manager 250, as described below with reference to FIGS. 6A to 9C, may calculate similarities among scattered light signals at points in time of detection of the collected learning data. Also, a scattered light signal which does not satisfy a reference similarity may be excluded using the calculated similarity and the scattering coefficient may be calculated using other scattered light signals. Also, a correlation coefficient between the scattering coefficient and the substance-in-blood numerical value may be obtained using an algorithm for obtaining a correlation coefficient, for example, a Pearson correlation coefficient algorithm, and the reference similarity may be adjusted until the correlation coefficient becomes a certain threshold or more.

The reference manager 250 may determine a reference similarity by repeatedly performing such a process and may update an existing reference similarity using the determined reference similarity. Also, when the reference similarity is updated, a correlation is derived using a scattering coefficient of scattered light signals satisfying the updated reference similarity and an actual substance-in-blood reference value, thereby obtaining a correlation model.

Meanwhile, the reference manager 250 may initially register a user to allow the user to use the apparatus 100 for estimating a substance in blood or may control the optical measurer 110 to sequentially detect a light signal for a predetermined time at predetermined time intervals according to a request of the user or a preset period. Also, the reference manager 250 may aggregate the number or rate of failing to satisfy the reference similarity when the similarity determiner 220 determines a similarity and may determine that an update of reference information is necessary and may control the optical measurer 110 when the aggregated number or rate is a certain threshold or more.

Figure 3:
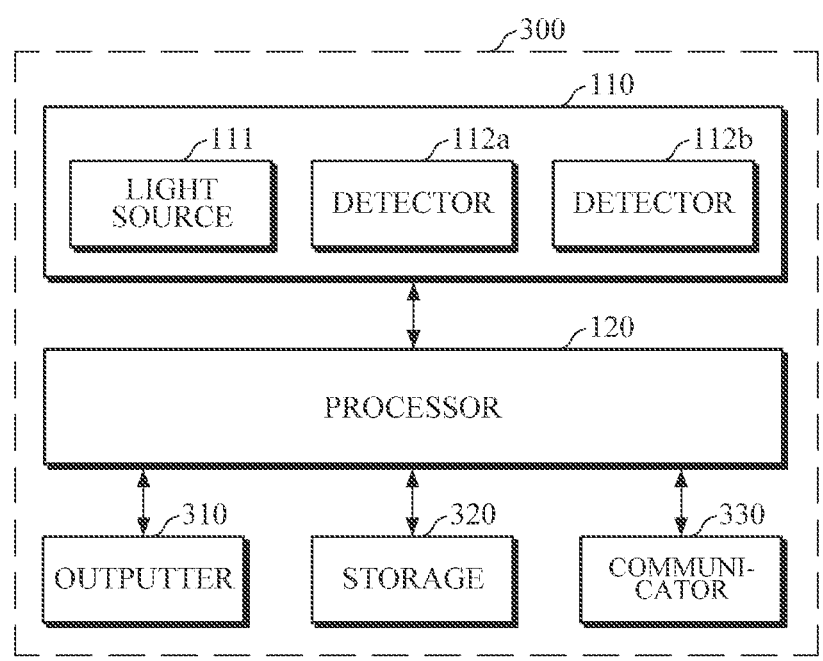
FIG. 3 is a block diagram illustrating another example of an apparatus for estimating a substance in blood.

FIG. 3 is a block diagram illustrating another example of an apparatus for estimating a substance in blood.

Referring to FIG. 3, an apparatus 300 for estimating a substance in blood may include an optical measurer 110, a processor 120, an outputter 310, a storage 320, and a communicator 330.

As described with reference to FIG. 1, the optical measurer 110 may include the light source 111 which emits light to the skin of the user and the plurality of detectors 112a and 112b which detect scattered light returning from the skin of the user. Also, the processor 120 may estimate a substance-in-blood such as neutral fat using detected scattered light signals. A detailed description is same as described above and will be omitted.

The outputter 310 may provide a processing result of the processor 120 to the user using various output means, for example, a display, a speaker, a haptic apparatus, etc. Here, the outputter 310 may visually/nonvisually output depending on the output means. Here, the processing result may include a result of estimating a substance in blood, a warning, alarm information, etc.

The storage 320 may be any one of the storage devices described above, may store reference information such as a reference similarity or correlation model information referred by the processor 120 and user information, and may store substance-in-blood information estimated by the processor 120, and an alarm, a warning, a history of estimating a substance in blood, and various pieces of statistic information generated based on the substance-in-blood information.

The communicator 330 may be a communication module embodied using various communication technologies. Here, the communication technologies may include, for example, Bluetooth communication, Bluetooth low energy (BLE) communication, near field communication (NFC), a wireless local area network (WLAN) communication, Zigbee communication, infrared data association (IrDA) communication, wireless fidelity (Wi-Fi) direct (WFD) communication, ultra wideband (UWB) communication, Ant+ communication, Wi-Fi communication, 3G, 4G, and 5G communication technologies but are not limited thereto.

The communicator 330 may be connected to various external apparatuses including an invasive substance-in-blood estimation apparatus to transmit and receive data. For example, information on a substance-in-blood numerical value actually measured from a blood sample of the user may be received from the invasive substance-in-blood estimation apparatus. Here, when it is determined that an update of the reference information is necessary, the processor 120 controls the communicator 330 to receive the actual substance-in-blood numerical value information from the invasive substance-in-blood estimation apparatus.

FIGS. 4A to 9C are views illustrating an example of processing of scattered light signals.

Figure 4A:
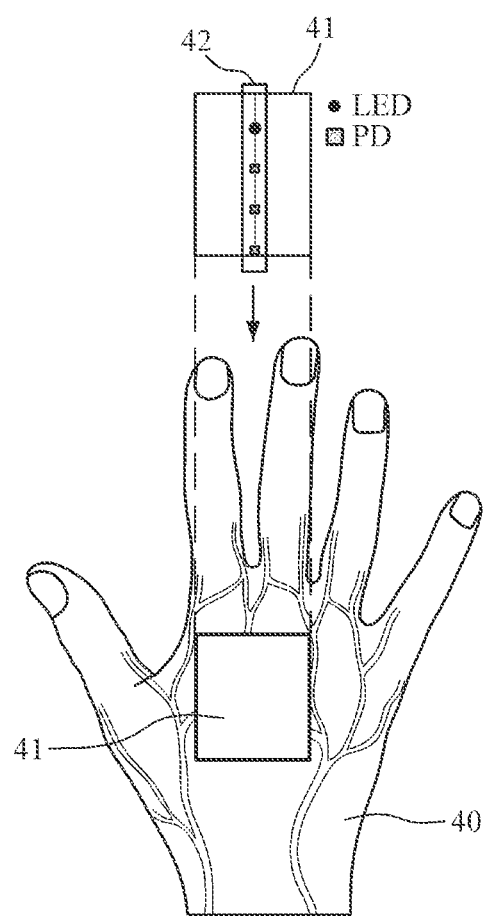
FIGS. 4A, 4B, 5A, 5B, 5C, 6A, 6B, 7A, 7B, 8A, 8B, 9A, 9B, and 9C are views illustrating examples of processing of scattered light signals.

FIG. 4A illustrates an example in which a configuration of the optical measurer 110 described above is embodied as one detection sensor 41 and in contact with a position of venous blood 42 of the back 40 of a hand. As shown in FIG. 4A, the detection sensor 41 may include one light source LED and a plurality of detectors PD. Also, the back 40 of a hand is shown as an example of a subject but is not limited thereto and the example may be an upper skin area of a wrist. In this case, the detection sensor 41 may be embodied to be in contact with a position of venous blood or capillaries at an upper portion of the wrist to measure scattered light from skin of the upper portion of the wrist.

Figure 4B:
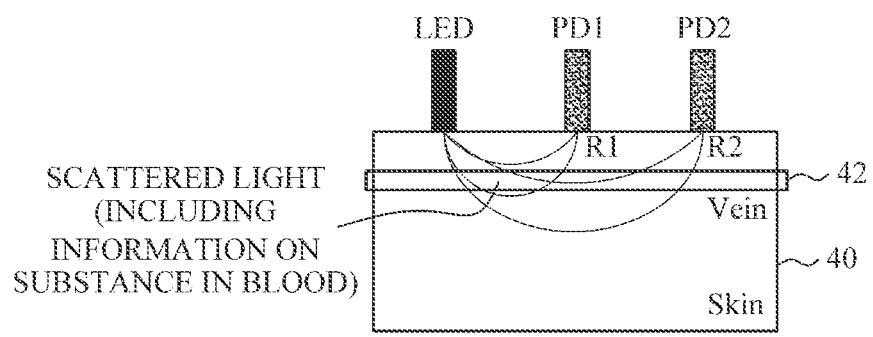

FIG. 4B illustrates an example in which the light source LED and two detectors PD1 and PD2 are disposed side by side in contact with the skin 40 to detect scattered light. Here, a first detector PD1 is positioned at position p1 and a second detector PD2 is positioned at position p2. The light source LED is disposed to be closer to the position p1 than the position p2. Light emitted by the light source LED to the skin 40 is scattered by a substance in the venous blood 42, and scattered light signals R1 and R2 which are scattered and return from the skin 40 may be detected by the first detector PD1 and the second detector PD2 at the same time.

Figure 5A:
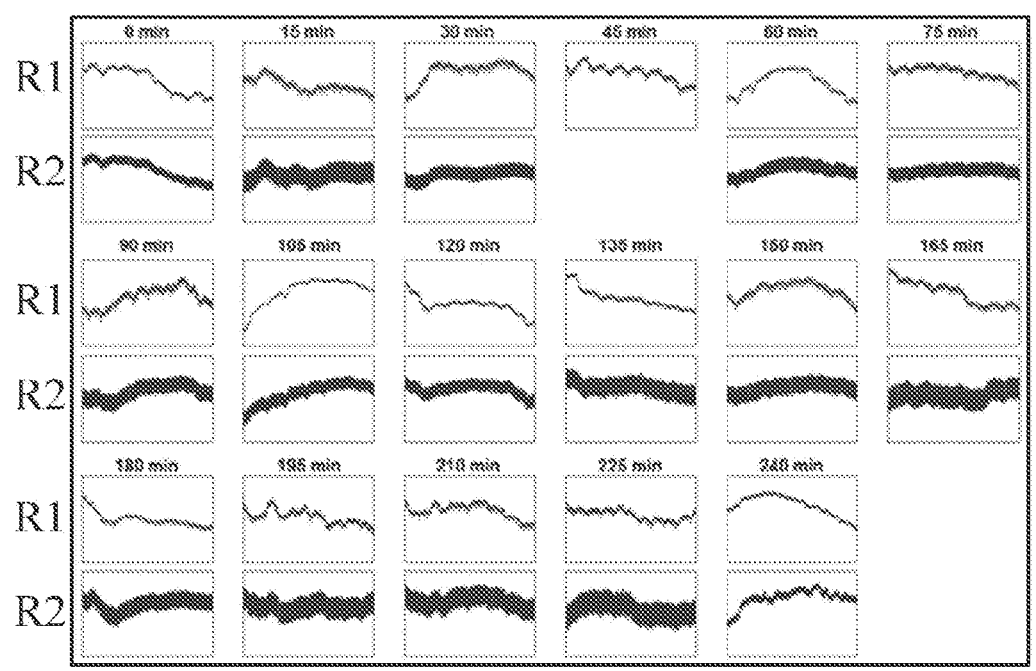

FIG. 5A illustrates a scattered light signal R1 detected by the first detector PD1 and a scattered light signal R2 detected by the second detector PD2 which are detected for 4 hours at 15 minute intervals through the example of FIG. 4B. An X axis of each of graphs shown in FIG. 5A indicates elapsed time, and a Y axis indicates the intensity of a scattered light signal. Here, since a slight time difference exists between points in time of detecting the scattered light signals R1 and R2, the points in time may be matched based on properties of the scattered light signals, for example, a peak, an inclination, etc.

Figure 5B:
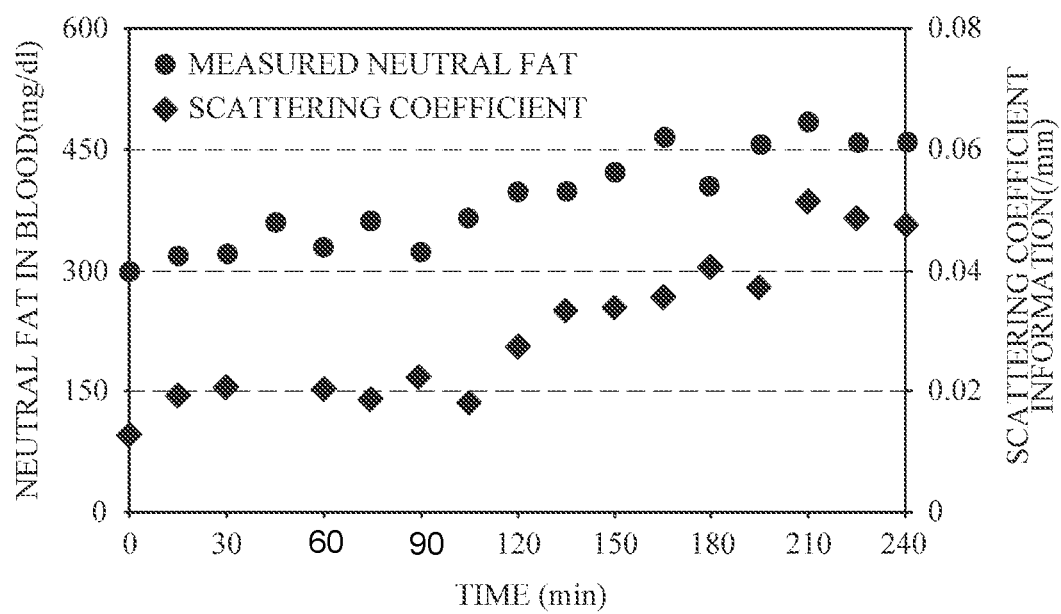
Figure 5C:
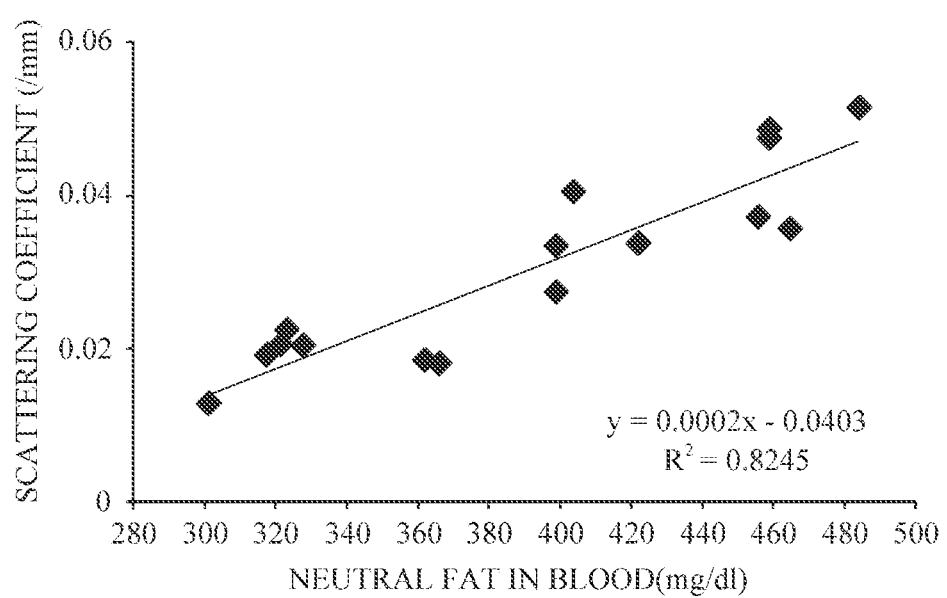

FIG. 5B is a graph illustrating a correlation between a scattering coefficient in a diamond shape of the scattered light signals R1 and R2 detected as shown in FIG. 5A and neutral fat in a circular shape actually measured from a blood sample of the user. An X axis of the graph indicates elapsed time, a left side of a Y axis indicates an actual numerical value of neutral fat in blood, and a right side of the Y axis indicates a calculated scattering coefficient. Here, the scattering coefficient may be calculated for each detection point in time and the actual numerical value of neutral fat in blood may be measured by an invasive neutral fat measuring apparatus according to points in time of detecting scattered light signals. FIG. 5C is a graph illustrating a correlation model derived as an equation form such as following Equation 1 based on a correlation between the scattering coefficient and the actual substance in blood in FIG. 5B.

$$y=0.0002x-0.0403 \quad \text{[Equation 1]}$$

Meanwhile, the example of FIGS. 5A to 5C may be performed by the reference manager 250 of FIG. 2B. For example, when generation and update of reference information is necessary, the reference manager 250 may obtain learning data from scattered light signals for a certain time shown in FIG. 5 by controlling a detection sensor, may calculate a scattering coefficient using the scattered light signals of the learning data as shown in FIGS. 5B and 5C, and may generate a correlation model using the calculated scattering coefficient and an actual substance-in-blood numerical value.

Figure 6A:
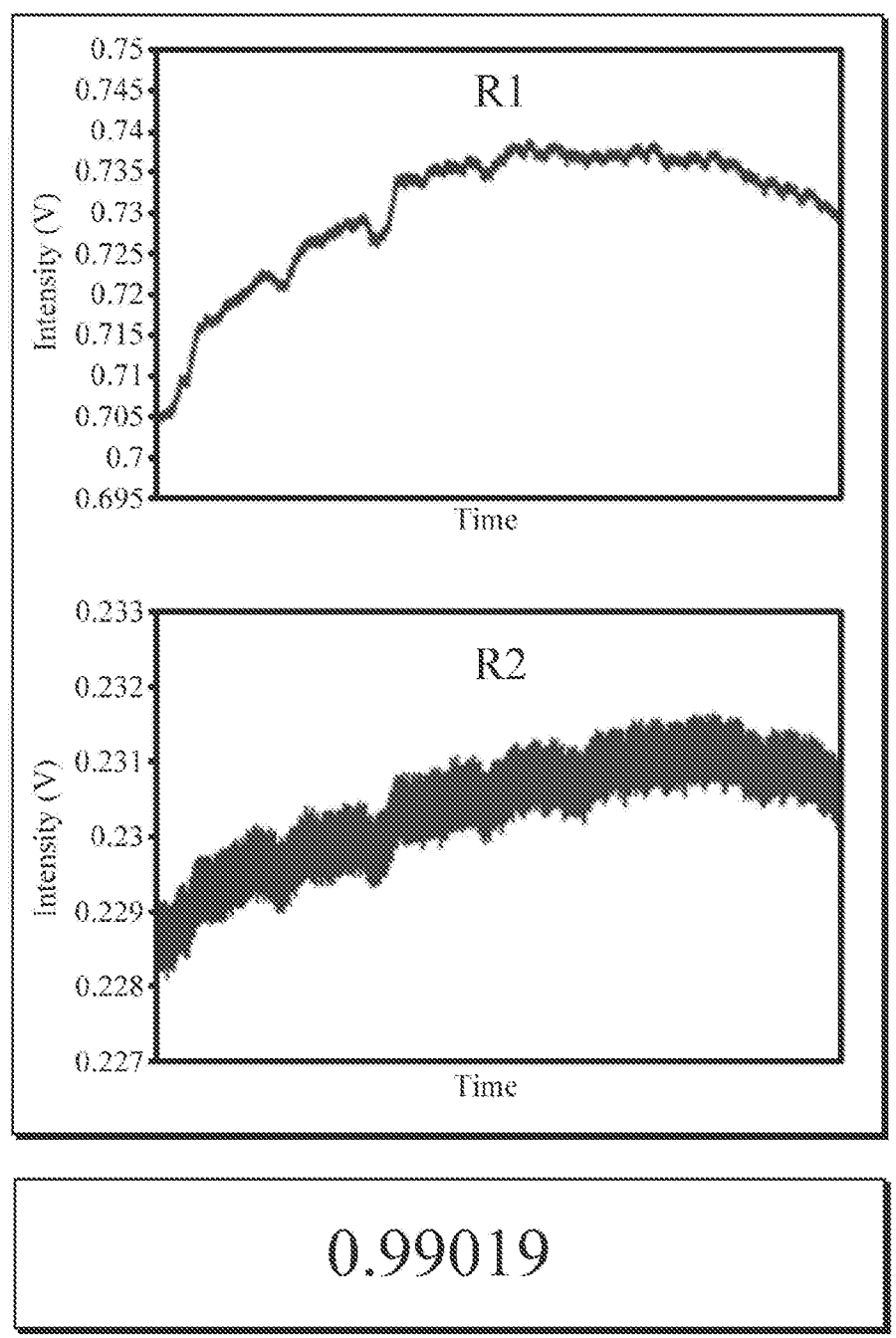
Figure 6B:
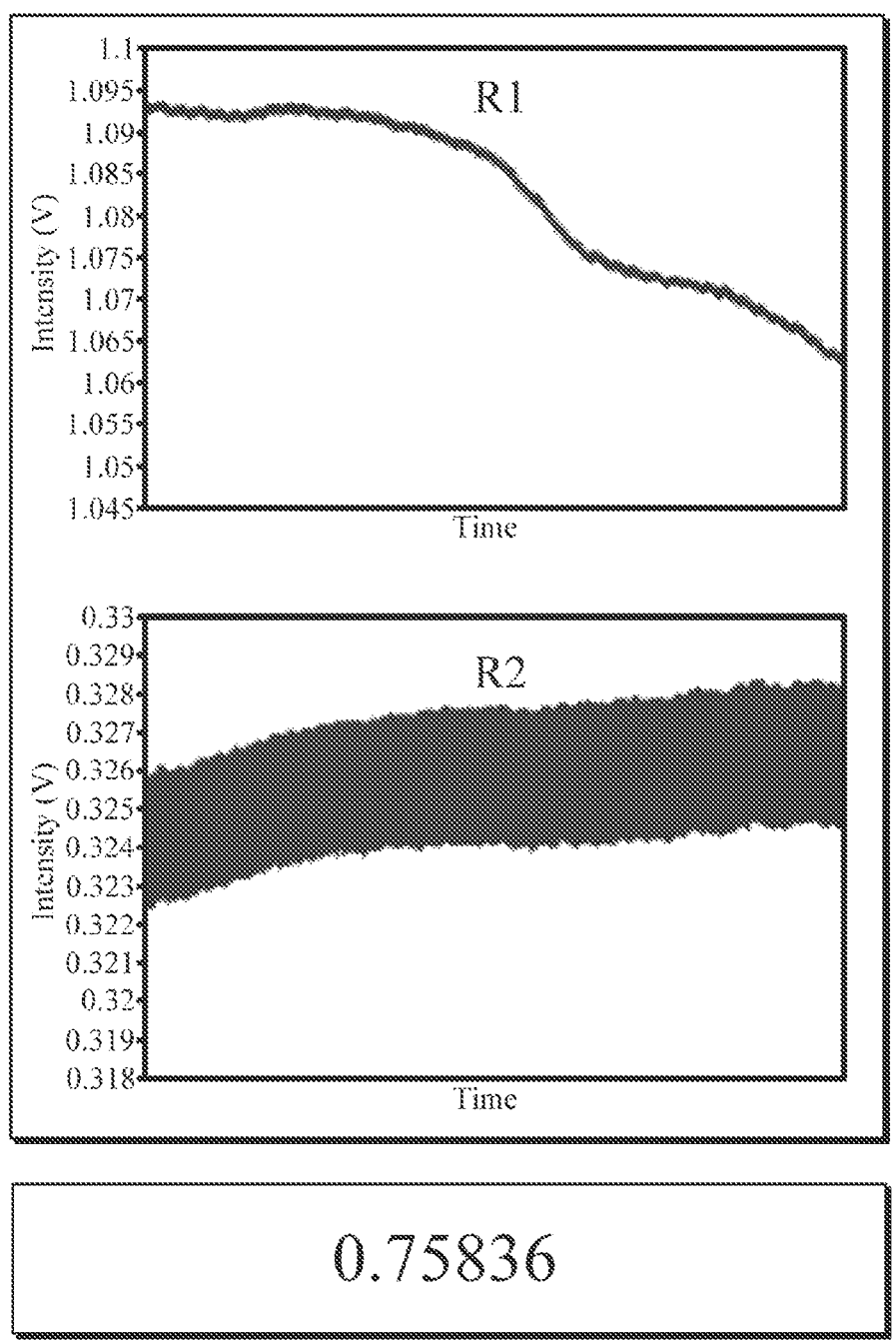

FIGS. 6A and 6B illustrate an example of calculating a similarity between the two light signals R1 and R2 using a cosine similarity algorithm. Referring to FIG. 6A, it may be known that directionalities of waveforms of the two light signals R1 and R2 as time passes are shown similar, and accordingly, a cosine similarity is calculated as a high value of 0.99019. On the contrary, referring to FIG. 6B, directionalities of waveforms as time passes are shown opposite, and accordingly, a cosine similarity is calculated as a relatively low value of 0.75836.

Figure 7A:
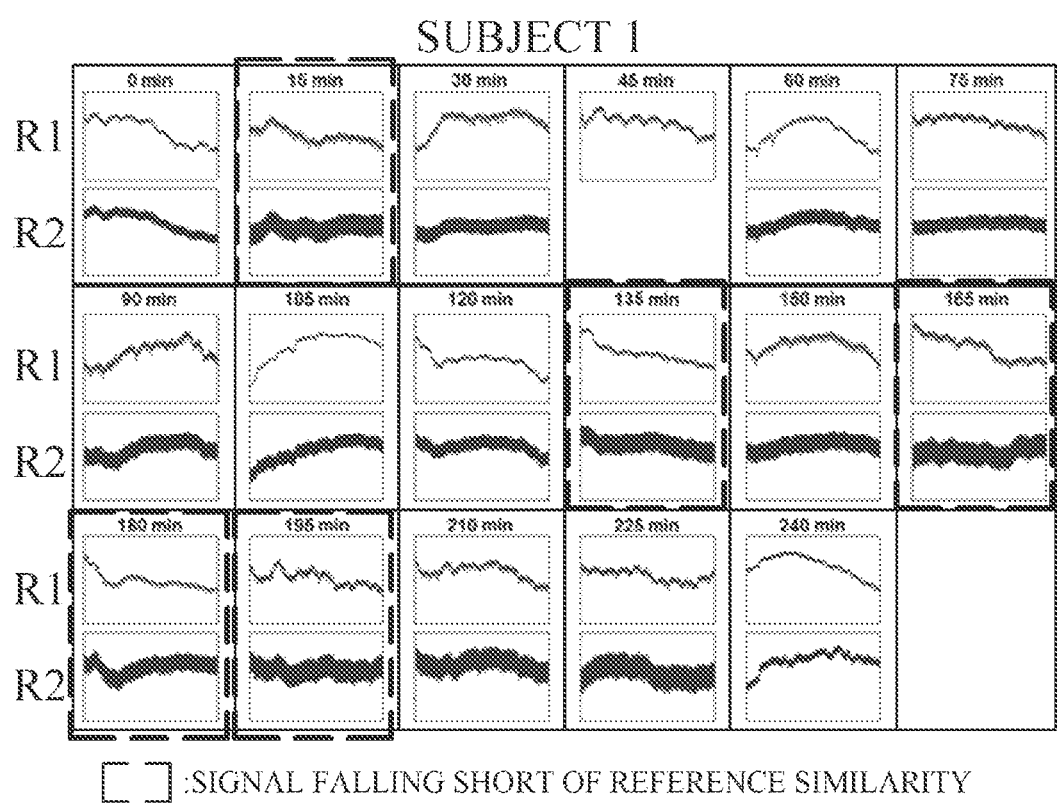
Figure 7B:
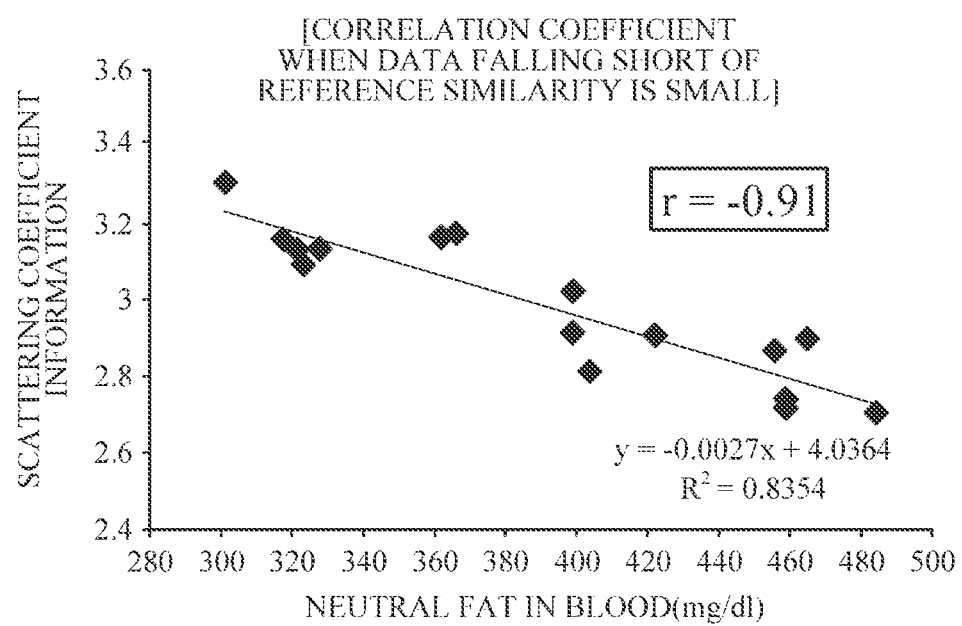

FIGS. 7A and 7B illustrate a correlation between a scattering coefficient derived using scattered light signal data measured from a subject 1 for 4 hours at 15 minute intervals and numerical values of neutral fat in blood measured at the same time. Referring to FIG. 7A, scattered light signals detected at relatively small 5 points in time of detection (at 15, 135, 165, 180, and 195 minutes) do not satisfy a reference similarity. Referring to FIG. 7B, it may be known that a correlation between a scattering coefficient calculated when a rate of data which does not satisfy the reference similarity in all data is relatively small and the numerical value of neutral fat in blood is high.

Figure 8A:
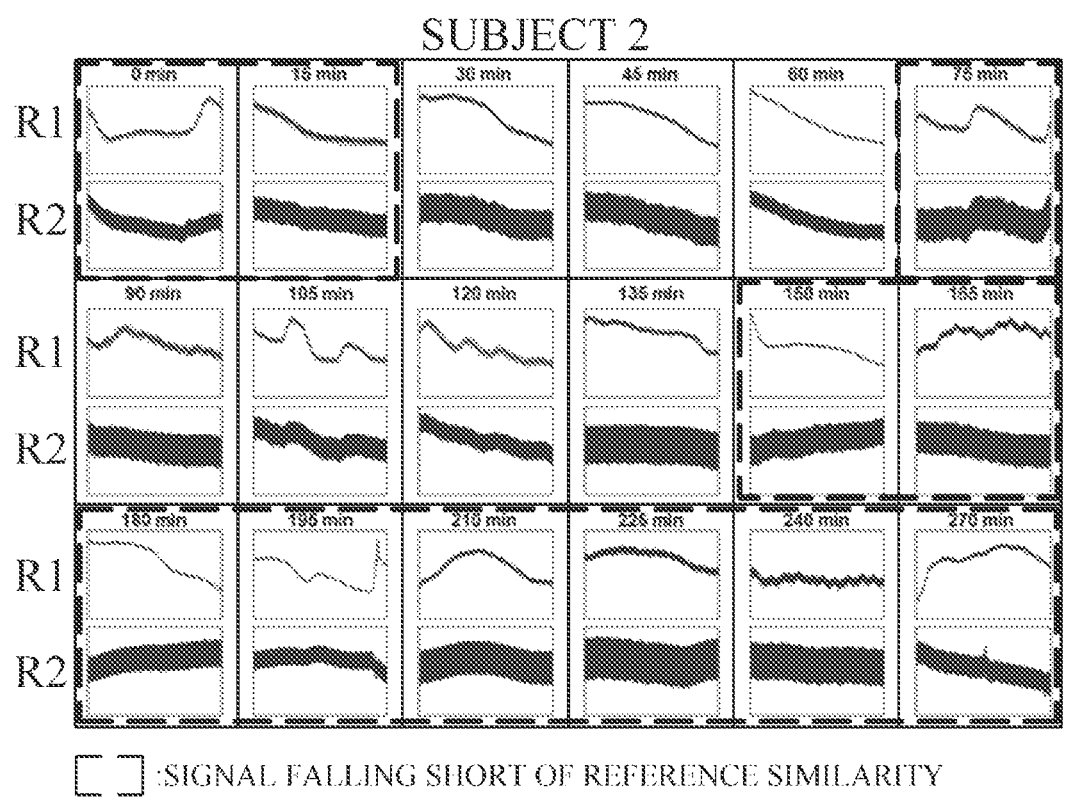
Figure 8B:
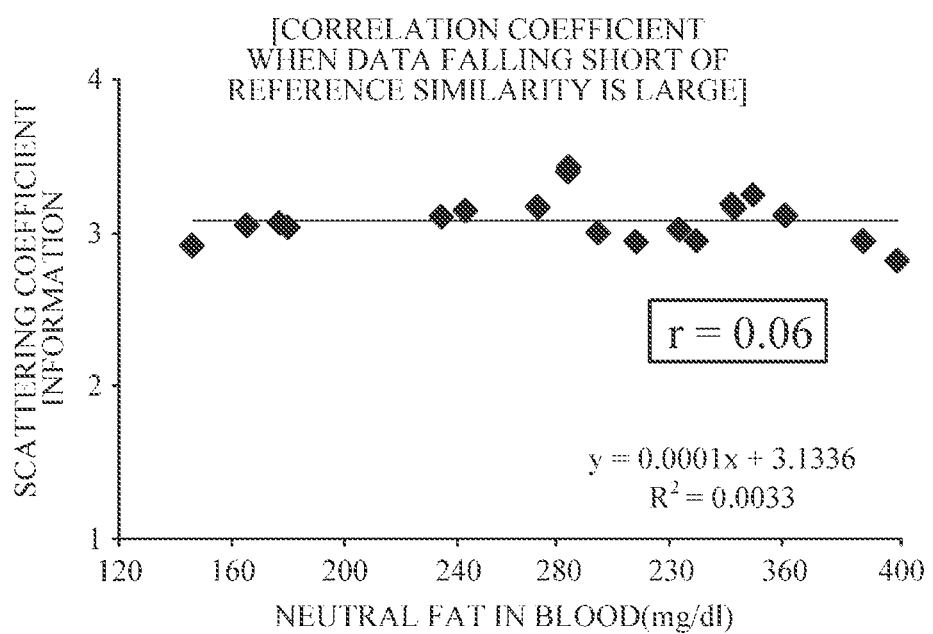

FIGS. 8A and 8B illustrate a correlation between a scattering coefficient and a numerical value of neutral fat in blood using scattered light signal data measured from a subject 2 for 4 hours at 15 minute intervals. Referring to FIG. 8A, similarities of scattered light signals detected at relatively many 11 points in time of detection (at 0, 15, 75, 150, 165, 180, 195, 210, 225, 240, and 270 minutes) do not satisfy a reference similarity. Referring to FIG. 8B, it may be known that a correlation between a scattering coefficient calculated when a rate of data which does not satisfy the reference similarity in all data is relatively large and the numerical value of neutral fat in blood is low.

Figure 9A:
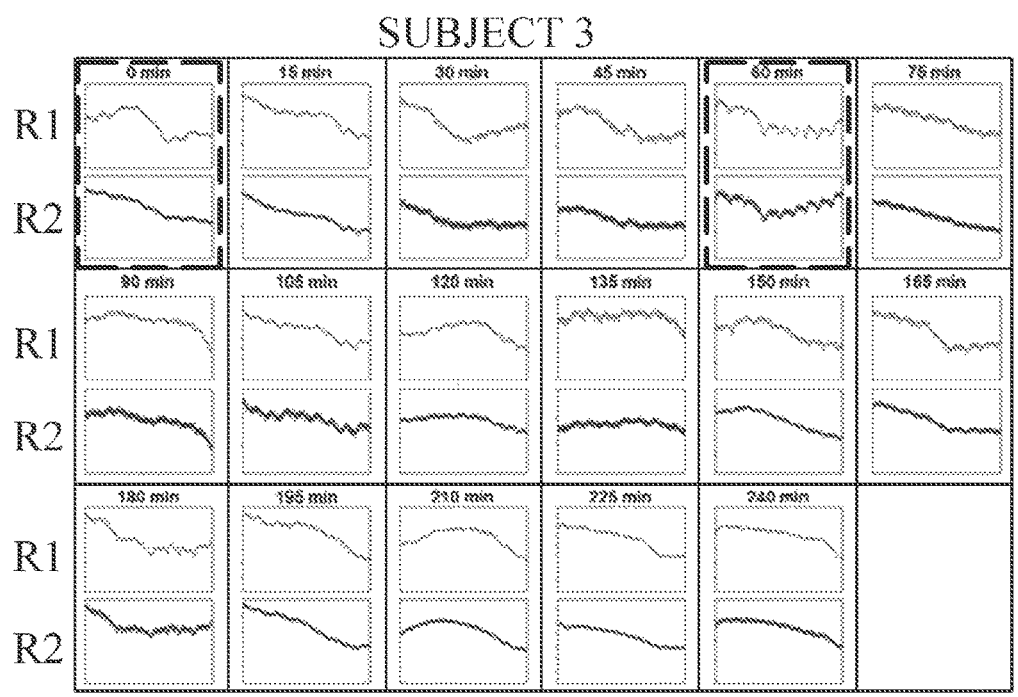
Figure 9B:
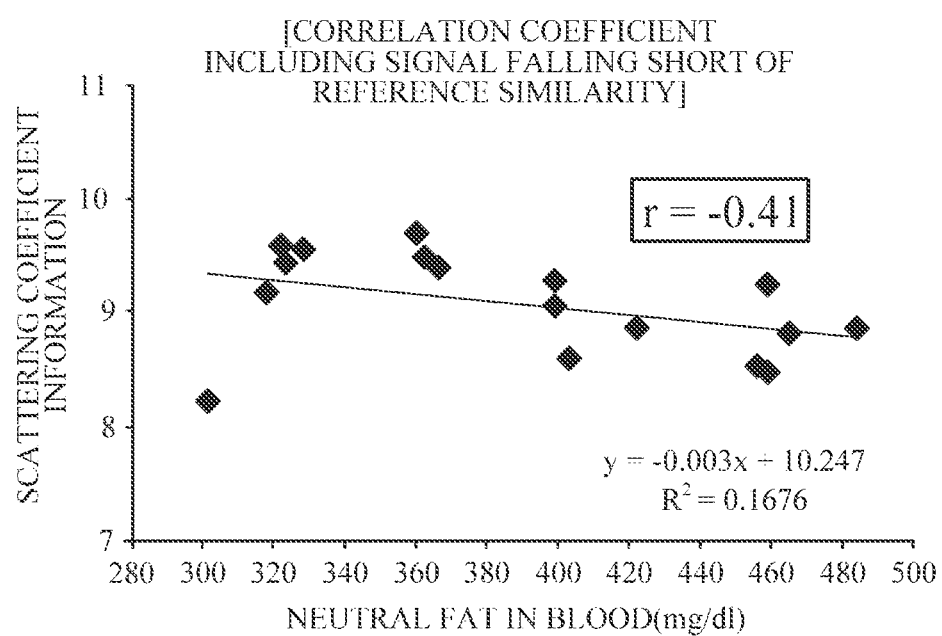
Figure 9C:
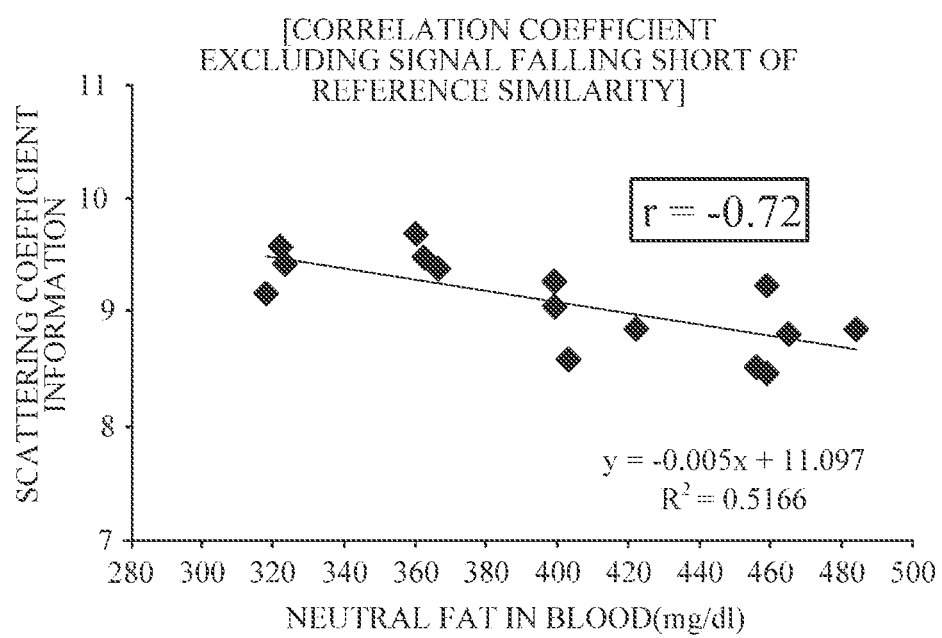

FIGS. 9A to 9C illustrate an example in which scattered light signal data of two points in time of detection (0 and 60 minutes) among scattered light signal data measured from a subject 3 for 4 hours at 15 minute intervals do not satisfy a reference similarity. When a correlation between a scattering coefficient and neutral fat in blood is obtained including signal data which fall short of a reference similarity as shown in FIG. 9B, a Pearson correlation coefficient is calculated −0.41. When a correlation is obtained excluding signals which fall short of the reference similarity, a correlation coefficient is calculated −0.72. Accordingly, it may be known that a more precise correlation is derived when signals which fall short of the reference similarity are excluded.

As described above with reference to FIGS. 4A to 9C, a scattered light signal is generally influenced from deformation of skin in contact with the detection sensor 41, a change of a measuring position according to the movement of the user, a distance between the light source LED and each of the detectors PD1 and PD2, etc. When a scattered light signal detected without considering such conditions is directly used, a wrong scattering coefficient may be calculated and consequently the accuracy of an estimate of a substance in blood may be decreased. According to the exemplary embodiment, since it is determined using a similarity between detected scattered light signals whether to use, a highly reliable estimation result of the substance in blood may be obtained. Also, when a scattering coefficient is calculated to generate or update a reference similarity or a correlation model, inappropriate scattered light signals are excluded based on similarities, thereby generating a correlation model with a higher correlation or a reference similarity.

Figure 10:
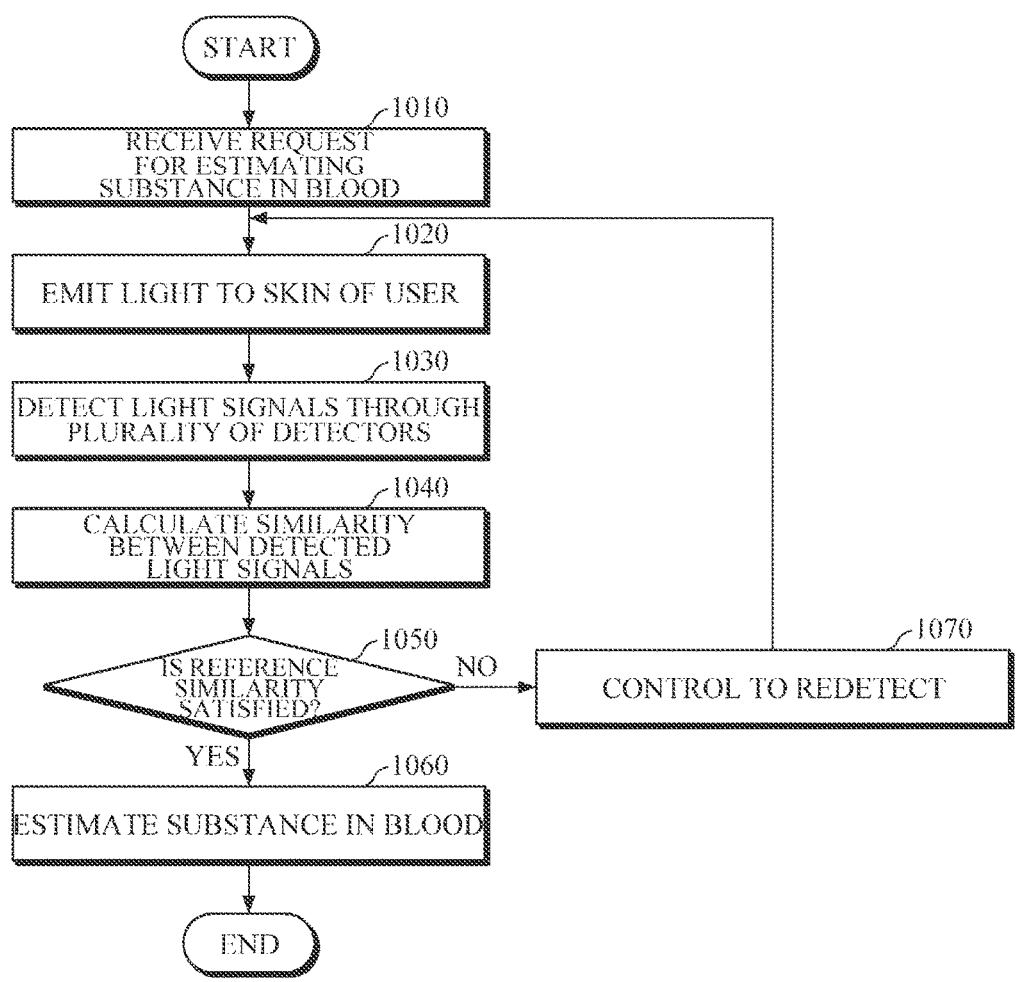
FIG. 10 is a flowchart illustrating an example method of estimating a substance in blood.

FIG. 10 is a flowchart illustrating an example method of estimating a substance in blood.

The method of estimating a substance in blood in FIG. 10 may be performed by the apparatuses 100 and 300 for estimating a substance in blood according to the embodiments shown in FIGS. 1 and 3.

First, when a request for estimating a substance in blood is received (operation 1010), a light source is driven to emit light to skin of a user (operation 1020) and scattered light signals returning from the skin of the user may be detected by a plurality of detectors (operation 1030). Here, the request for estimating a substance in blood may be received from the user. Also, the light source may be a single LED light source which emits light in a near infrared bandwidth.

Next, a similarity may be calculated among light signals detected by the plurality of detectors (operation 1040). Here, the similarity may be a cosine similarity for determining whether directionalities of waveforms on a time axis are similar. However, the similarity is not limited thereto.

After that, when the similarity is calculated, it is determined whether the similarity satisfies a preset reference similarity (operation 1050). When a detected scattered light signal satisfies the reference similarity, the substance in blood may be estimated using the intensity of the scattered light signal (operation 1060). Here, a scattering coefficient defined as a rate the intensity of the detected scattered light signal or a value proportional to the rate may be calculated, and the substance in blood may be estimated using the calculated scattering coefficient and a correlation model.

In operation 1050, when the reference similarity is not satisfied, the light source is controlled again to measure scattered light signals again (operation 1070).

Figure 11:
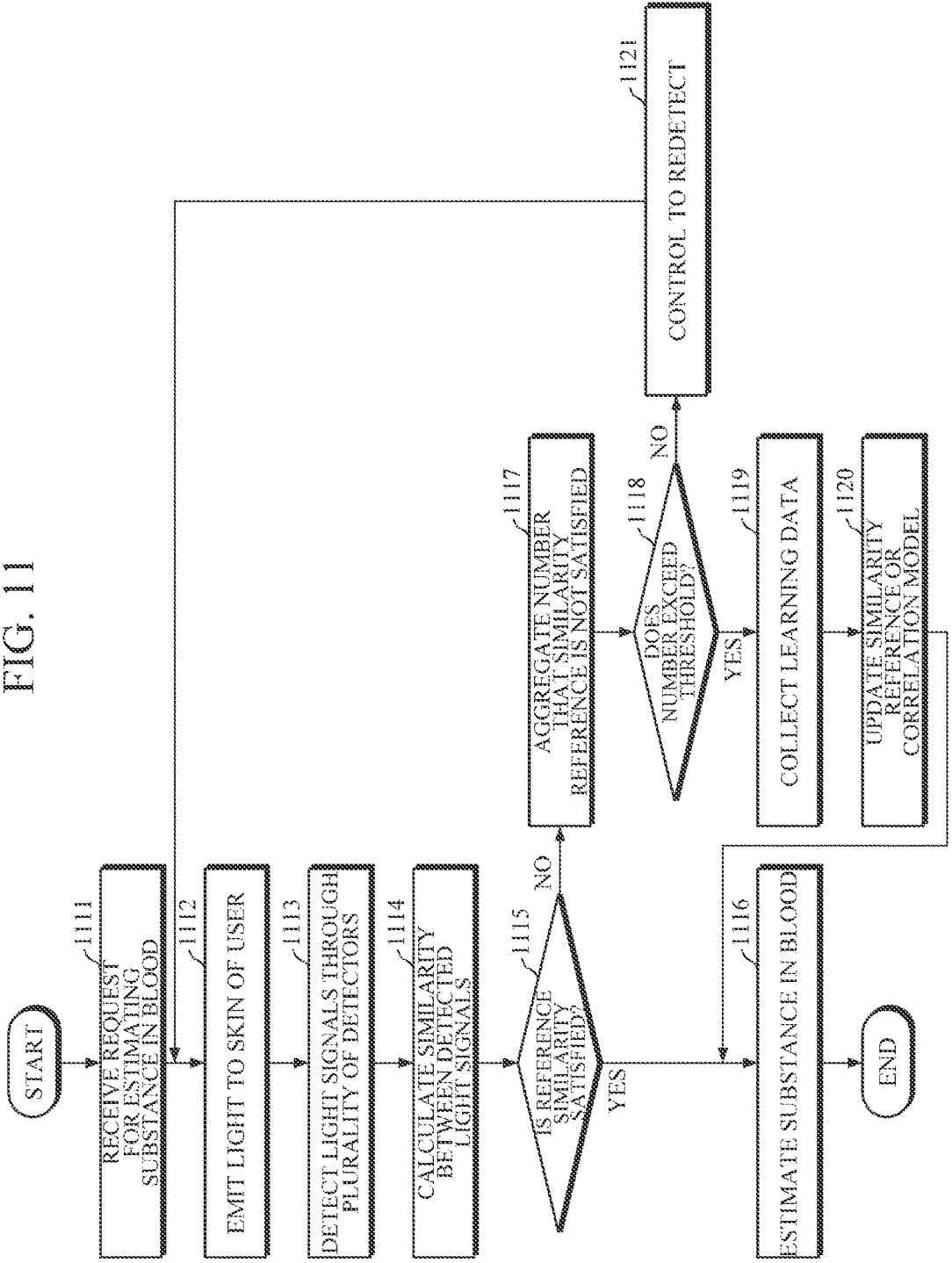
FIG. 11 is a flowchart illustrating another example method of estimating a substance in blood.

FIG. 11 is a flowchart illustrating another example method of estimating a substance in blood.

The method of FIG. 11 may be another embodiment performed by the apparatuses 100 and 300 for estimating a substance in blood according to the exemplary embodiments of FIGS. 1 and 3.

First, when a request for estimating a substance in blood is received (operation 1111), a light source is driven to emit light to skin of a user (operation 1112) and scattered light signals returning from the skin of the user may be detected by a plurality of detectors (operation 1113).

After that, a similarity between light signals detected by the plurality of detectors is calculated (operation 1114) and it may be determined whether the calculated similarity satisfies a preset reference similarity (operation 1115).

As a result of the determination in operation 1115, when the detected scattered light signal satisfies the reference similarity, the substance in blood may be estimated using the intensity of the scattered light signal (operation 1116). Here, a scattering coefficient defined as a rate the intensity of the detected scattered light signal or a value proportional to the rate may be calculated, and the substance in blood may be estimated using the calculated scattering coefficient and a correlation model.

In operation 1115, when the reference similarity is not satisfied, the number of not satisfying the reference similarity is aggregated (operation 1117) and it may be determined whether the aggregated number exceeds a preset threshold (operation 1118). When the aggregated number exceeds the threshold as a result of the determination, an update of the reference similarity or the correlation model may be determined to be necessary and learning data may be collected (operation 1119). Here, the light source and the plurality of detectors may be controlled for a certain time for collecting the learning data to obtain the learning data from scattered light signal data at certain time intervals.

After that, reference information such as the reference similarity, correlation model, etc. may be updated using the collected learning data (operation 1120). Here, a correlation between a scattering coefficient and a numerical value of a substance in blood of the learning data may be derived using information on a numerical value of a substance in blood actually measured by an invasive substance-in-blood estimation apparatus from a blood sample of the user and the correlation model may be updated using the derived correlation.

As a result of the determination in operation 1118, when the aggregated number does not exceed the threshold, it may be determined that the update of the reference information is unnecessary and redetection of scattered light signals may be controlled (operation 1121).

Figure 12:
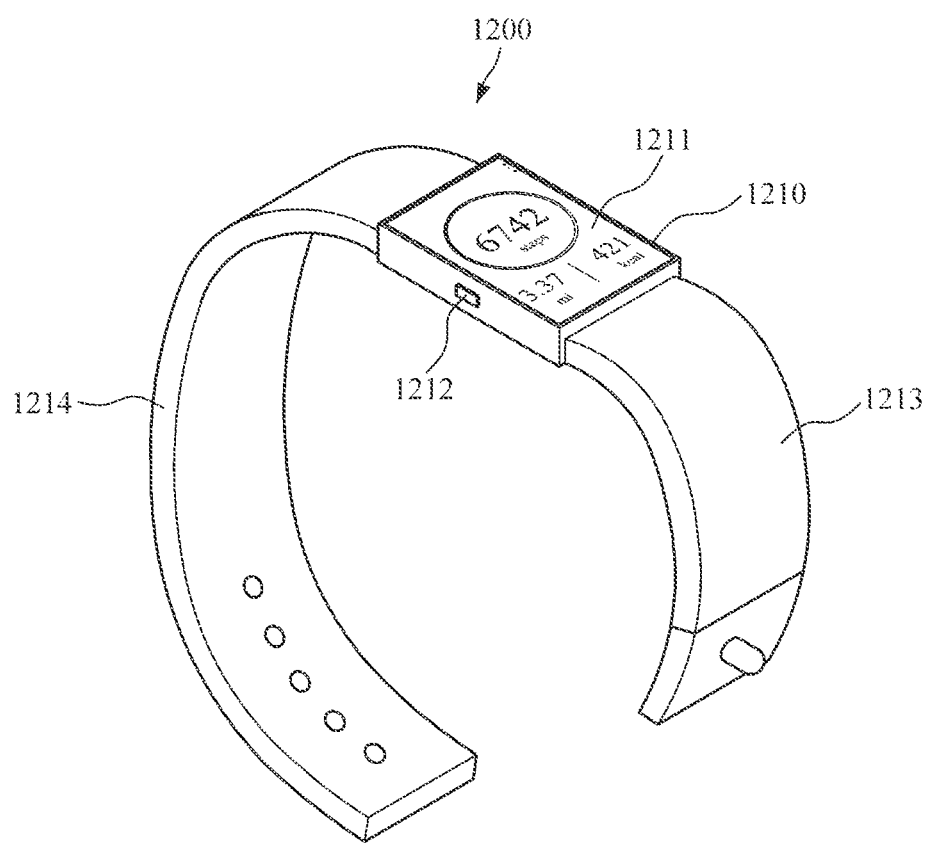
FIG. 12 is a schematic diagram illustrating an example of a wearable device.
Figure 13:
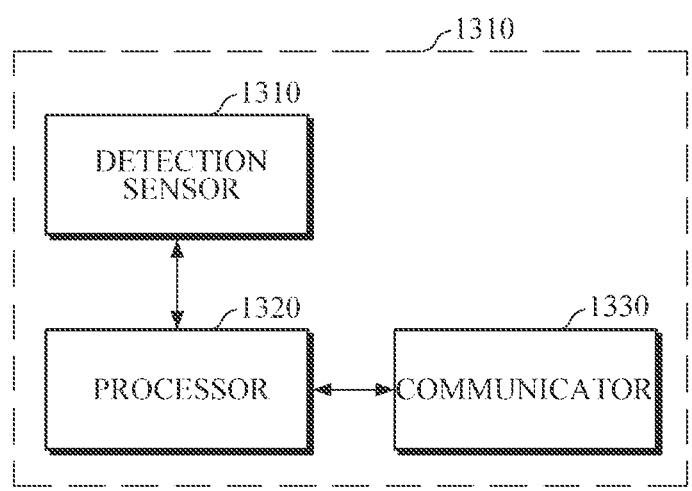
FIG. 13 is a block diagram illustrating an example of a wearable device.

FIG. 12 is a schematic diagram illustrating an example of a wearable device. FIG. 13 is a block diagram illustrating an example of a wearable device. As shown in FIGS. 12 and 13, the apparatuses for estimating a substance in blood described above, for example, various embodiments for estimating neutral fat in blood may be installed in smart band type wearable devices. However, since it is merely an example for convenience of description, it should be understood that the embodiments are not limited to smart band type wearable devices.

Referring to FIGS. 12 and 13, a wearable device 1200 may include a device body 1210 and a strap including strap members 1213 and 1214.

The strap may be flexible and may be bent like a shape surrounding a wrist of a user or bent like a shape separated from the wrist of the user. Here, a battery which supplies power to the wearable device 1200 may be built in the device body 1210 or the strap member 1214.

Also, the device body 1210 of the wearable device 1200 may internally include a detection sensor 1310 which emits light to skin of the user and detects light signals scattered from the skin and returning, and a processor 1320 which estimates a substance in blood of the user using the scattered light signals measured by the detection sensor 1310.

The detection sensor 1310 may be attached to a bottom portion of the device body 1210, for example a portion in contact with the wrist of the user and may include a light source which emits light to the skin of the user according to a control signal of the processor 1320 and a plurality of detectors which are arranged side by side at different distances from the light source and detect light signals returning from the skin of the user. Here, the light source may be configured to emit light in a near infrared bandwidth.

The processor 1320 may generate a control signal according to a request for estimating a substance in blood of the user and may control the detection sensor 1310. Also, when the detection sensor 1310 obtains scattered light signals, the processor 1320 may receive scattered light signal data from the detection sensor 1310 and may estimate the substance in blood of the user using the received scattered light signal data. For example, the processor 1320 may calculate a similarity between scattered light signals detected by the plurality of detectors, may estimate the substance in blood when the calculated similarity satisfies a preset reference similarity, and may control the detection sensor 1310 again to redetect scattered light signals when the preset reference similarity is not satisfied.

When the similarity of the detected scattered light signals satisfies the reference similarity, the processor 1320 may calculate a scattering coefficient using the scattered light signals and may estimate a substance in blood using the calculated scattering coefficient and a correlation model.

Also, the processor 1320 may generate additional information necessary for health care such as alarm or warning information on whether neutral fat exceeds a reference, provided to the user, or a change in health condition, etc. based on the estimated substance in blood, for example, neutral fat information.

Also, the wearable device 1200 may further include an operation portion 1212 and a displayer 1211 mounted on the device body 1210.

The operation portion 1212 may receive and transmit a control command of the user to the processor 1320 and may include a power button for inputting a command for turning on/off power of the wearable device 1200.

The displayer 1211 may display and provide estimated neutral fat information, etc. to the user under the control of the processor 1320. Here, the displayer 1211 may display additional information such as the neutral fat information, an alarm, a warning, etc. to the user in various visual/nonvisual manners.

Also, the device body 1210 may further include a communicator 1330 in an inner space thereof to communicate with external apparatuses such as a portable terminal of the user, an invasive substance-in-blood estimation apparatus, a substance-in-blood management apparatus, etc.

The communicator 1330 may transmit necessary information to the portable terminal of the user with relatively excellent computing performance to provide the information to the user under the control of the processor 1320. Also, when the processor 1320 determines that an update of reference information is necessary and sets an estimation mode of the detection sensor 1310 as a reference management mode, the invasive substance-in-blood estimation apparatus may be connected to receive an actual reference value of the substance in blood necessary for updating the reference information.

While not restricted thereto, an exemplary embodiment may be embodied as a computer-readable code in a computer-readable recording medium. The computer-readable recording medium includes all types of recording media in which computer readable data are stored.

Examples of the computer-readable recording medium include an ROM, an RAM, a CD-ROM, a magnetic tape, a floppy disk, an optical data storage device, etc. Further, the computer-readable recording medium may be implemented in the form of a carrier wave such as Internet transmission. In addition, the computer-readable recording medium may be distributed to computer systems over a network, in which computer-readable codes may be stored and executed in a distributed manner. Also, functional programs, codes, code segments for performing the embodiments may be easily derived by programmers of ordinary skill in the art. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for estimating a substance in blood, the apparatus comprising:
    a light source configured to emit light to skin of a user;
    a plurality of detectors which are disposed at different distances from the light source and configured to detect light signals from the light returning from the skin; and
    a processor configured to determine a similarity between at least two light signals detected at the different distances from the light source, among the detected light signals, determine whether the determined similarity is greater than or equal to a reference similarity, and estimate an amount of the substance in blood based on the detected light signals when the determined similarity is greater than or equal to the reference similarity.

2. The apparatus of claim 1, wherein the processor is further configured to determine the similarity between waveforms of the at least two light signals based on a time axis.

3. The apparatus of claim 2, wherein the similarity comprises at least one of Euclidean distance, Pearson correlation coefficient, Spearman correlation coefficient, and a cosine similarity.

4. The apparatus of claim 1, wherein the light source comprises a near infrared (NIR) light emitting diode (LED) light source.

5. The apparatus of claim 1, wherein the processor is further configured to control to redetect light signals returning from the skin of the user when the determined similarity is less than the reference similarity.

6. The apparatus of claim 1, wherein the processor is further configured to determine scattering coefficients using light signals which have a similarity greater than the reference similarity, and obtain a level of the substance in blood based on the scattering coefficients and a correlation model.

7. The apparatus of claim 1, wherein when a number of the detected light signals that have similarities equal to or greater than the reference similarity is three or greater, the processor selects two light signals from the detected light signals based on similarities among the detected light signals and estimates the amount of the substance in blood using the selected two light signals.

8. The apparatus of claim 1, wherein the processor is further configured to update reference information which comprises at least one of the reference similarity and a correlation model.

9. The apparatus of claim 8, wherein the processor is further configured to aggregate a number of times that the determined similarity is less than the reference similarity and updates the reference information when the aggregated number exceeds a threshold.

10. The apparatus of claim 8, wherein the processor is further configured to collect learning data using the detected light signals and update the reference information based on the collected learning data.

11. The apparatus of claim 8, further comprising a communicator which is connected to an external apparatus and receives a reference value of the substance in blood measured from the blood of the user,
    wherein the processor is further configured to update the reference information based on the received reference value of the substance in blood.

12. The apparatus of claim 1, wherein the substance in blood comprises at least one of blood sugar, cholesterol, neutral fat, protein, and uric acid.

13. The apparatus of claim 1, further comprising an outputter which outputs a result of estimating the substance in blood to the user.

* * * * *